United States Patent
Ehrenreich et al.

(10) Patent No.: US 8,366,659 B2
(45) Date of Patent: Feb. 5, 2013

(54) REPERFUSION BALLOON INFLATION DEVICE

(75) Inventors: Kevin J. Ehrenreich, San Francisco, CA (US); Jesus Magana, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 176 days.

(21) Appl. No.: 13/032,743

(22) Filed: Feb. 23, 2011

(65) Prior Publication Data

US 2011/0270174 A1  Nov. 3, 2011

Related U.S. Application Data

(63) Continuation-in-part of application No. 12/771,968, filed on Apr. 30, 2010, and a continuation-in-part of application No. 12/771,946, filed on Apr. 30, 2010.

(51) Int. Cl.
*A61M 29/00* (2006.01)

(52) U.S. Cl. ................... 604/97.01; 604/98.01

(58) Field of Classification Search .... 604/99.01–99.02, 604/96.01, 97.01, 98.01
See application file for complete search history.

(56) References Cited

U.S. PATENT DOCUMENTS

| | | | |
|---|---|---|---|
| 4,740,203 A * | 4/1988 | Hoskins et al. | 604/191 |
| 5,011,468 A | 4/1991 | Lundquist et al. | |
| 5,336,184 A | 8/1994 | Teirstein | |
| 5,425,713 A | 6/1995 | Taylor et al. | |
| 6,746,465 B2 | 6/2004 | Diederich et al. | |
| 6,900,008 B2 | 5/2005 | Vinten-Johansen et al. | |
| 7,220,252 B2 | 5/2007 | Shah | |
| 7,686,781 B2 | 3/2010 | Vinten-Johansen | |
| 2003/0078538 A1 | 4/2003 | Neale et al. | |
| 2004/0111079 A1 | 6/2004 | Heyes et al. | |
| 2004/0255956 A1 | 12/2004 | Vinten-Johansen et al. | |
| 2005/0070848 A1 | 3/2005 | Kim et al. | |
| 2005/0118562 A1 | 6/2005 | Vinten-Johansen et al. | |
| 2006/0079573 A1 | 4/2006 | Vinten-Johansen et al. | |
| 2006/0100639 A1 | 5/2006 | Levin et al. | |
| 2006/0205671 A1 | 9/2006 | Vinten-Johansen | |
| 2007/0010847 A1 | 1/2007 | Pepper | |
| 2007/0142818 A1 | 6/2007 | Webler et al. | |
| 2007/0160645 A1 | 7/2007 | Vinten-Johansen | |

(Continued)

OTHER PUBLICATIONS

ISR/WO for PCT/US2010/033276 dated Jul. 30, 2010.

(Continued)

*Primary Examiner* — Nicholas Lucchesi
*Assistant Examiner* — Melissa A Snyder
(74) *Attorney, Agent, or Firm* — Lisa A. Chiarini; Walter M. Egbert, III; Hughes Hubbard & Reed LLP

(57) ABSTRACT

An ischemic postconditioning system and related method comprising a catheter including a plurality of lumens and at least one expandable member with at least one chamber including a moveable plunger and a return mechanism operatively engaged with the plunger. The moveable plunger divides the at least one chamber into first and second volumes. A first pressure source is provided having a first fluid at a first pressure and is disposed in fluid communication with the first volume of the chamber. Further, a second pressure source is provided having a second fluid at a second pressure and is disposed in fluid communication with the second volume of the chamber. Similarly, the at least one expandable member is disposed in fluid communication with the second volume of the chamber. The first fluid supplied by the first pressure source displaces the plunger in a first direction delivering at least a portion of the second fluid into the at least one expandable member. Also, the return mechanism displaces the plunger in a second direction delivering the second fluid from the second pressure source to the second volume of the chamber.

30 Claims, 8 Drawing Sheets

U.S. PATENT DOCUMENTS

2008/0097383 A1    4/2008    Vinten-Johansen
2008/0097385 A1    4/2008    Vinten-Johansen et al.
2009/0018498 A1    1/2009    Chiu et al.
2010/0082012 A1    4/2010    Hattangadi et al.

OTHER PUBLICATIONS

ISR/WO for PCT/US2010/033270 dated Jul. 9, 2010.
Poppenga et al., "Assessment of Potential Therapies for Acute T-2 Toxicosis in the Rat," 1987, Toxicon, vol. 25, No. 5, pp. 537-546, Department of Veterinary Biosciences, University of Illinois, Urbana, IL 61801, U.S.A.
Heng Zhao, "Ischemic Postconditioning as a Novel Avenue to Protect Against Brain Injury After Stroke" Journal of Cerebral Blood Flow & Metabolism (2009) 29, 873-885, Department of Neurosurgery, Stanford University School of Medicine, Stanford, California, U.S.A.

* cited by examiner

REPERFUSION BALLOON INFLATION DEVICE

CROSS REFERENCE TO RELATED APPLICATIONS

This application is a Continuation-In-Part of U.S. patent application Ser. No. 12/771,968 filed Apr. 30, 2010, and is a Continuation-In-Part of U.S. patent application Ser. No. 12/771,946, filed Apr. 30, 2010, the entirety of which is hereby incorporated by reference.

FIELD OF THE INVENTION

The invention relates to catheter systems. More particularly, the invention relates to a catheter having a plurality of lumens and a fluid circuit including a syringe chamber to permit rapid, sequential, inflation and deflation of an expandable member, such as a balloon, which is particularly useful in reducing the manifestation of reperfusion injury with postconditioning techniques.

BACKGROUND OF THE INVENTION

When a patient suffers from an ischemic event, the blood supply to tissues and organs distal to the blockage or occlusion is significantly diminished. The resulting deprivation of oxygen increases the risk of necrosis of the tissues and organs. Generally, a patient suffering an ischemic event is treated by minimally invasive catheterization, such as for example percutaneous transluminal coronary angioplasty (PCTA). PCTA is employed to dilate the ischemic blockage and to restore the blood supply to the tissues and organs. Rapid restoration of blood flow after an ischemic event minimizes the duration of insufficient oxygenation to the tissue and organs, and therefore optimizes tissue and organ survival. However, it has now been found that restoring blood supply in a rapid and consistent manner results in reperfusion injury. A shock to the tissues and organs from rapid oxygen re-saturation and abrupt changes to pH level in the tissue can results in an overall increase in the infarct size.

Reperfusion injury results from the rapid opening of a blood vessel such as those of the coronary, peripheral, and/or cerebral vasculature. For example, the rapid opening of an artery of the heart during a ST-Elevation Myocardial Infarction ("STEMI"), or an artery to the brain (ischemic stroke), or an artery to the other vital organs such as the kidney or liver or other tissues of the body sometimes causes ischemic injury in myocardial, cerebral, peripheral and spinal infarction, for example.

One method to reduce or prevent the occurrence of reperfusion injury is a technique known as postconditioning. Postconditioning is a method during which the blood flow in the infarcted artery is stopped and started for multiple cycles immediately after re-opening of initial flow from the STEMI. This re-opening of flow can be either before or after angioplasty, with or without placement of a stent. Currently, physicians typically use an angioplasty catheter to perform postconditioning. However, the use of an angioplasty catheter is not optimal. For example, the angioplasty balloon is not configured to quickly occlude flow. Instead, the angioplasty balloon is designed to carefully create a new, circular lumen. Additionally, the typical angioplasty balloon is non-compliant, meaning it is designed and/or made of a material that is meant to be inflated with a range of pressures, while not significantly changing its outer diameter size. A typical non-compliant angioplasty balloon becomes circular at approximately 4 atmospheres of pressure. As the balloon pressure is increased, the outer diameter grows very little even as pressure is increased to 14-18 atmospheres. Such characteristics can be drawbacks for postconditioning. Further, an angioplasty balloon is typically designed to open a stenosis or blood vessel along a lesion, rather than just occlude flow. Thus, the length of an angioplasty balloon is generally between 8 mm to 40 mm, while an occlusion balloon could be shorter.

Another major drawback to using an conventional angioplasty catheter for postconditioning is that prior to use, the physician must measure the artery, for example, by fluoroscopy, then size the balloon both for length and diameter, retrieve an appropriately sized balloon from inventory, and then go through various steps to prepare the balloon such as removing the air trapped within the balloon before filling the balloon with saline/contrast mixture. Thus, using the angioplasty catheter with the angioplasty balloon suffers from inefficiencies. Further, the angioplasty catheter typically must be manually actuated to both inflate and deflate the balloon. For example, the use of an angioplasty catheter for postconditioning usually requires rapid rotation of a screw piston in order to deliver the fluid in a controlled manner, while watching the pressure gage of an Indeflator. Inflation of the balloon to a circular size can require 10-20 twists of the Indeflator in order to expand the balloon. During deflation, the Indeflator is normally directly unlocked and rapidly deflated. If a controlled deflation is required, then the Indeflator can be manually screwed down to a lower pressure. Physician to physician variability will directly ensue, meaning that over the course of multiple inflations and deflations, there will be a great variability in the rise and fall of blood flow in the artery. Normalizing the blood flow, i.e. the rate of inflation, pressure of inflation, and rate of deflation across physicians can be critical to the efficacy of postconditioning. In addition to the cumbersome nature of actuating inflation and deflation of the angioplasty catheter, the speed of inflation is limited by the physical capability or limitations of the treating physician to rapidly rotate the screw piston. Given that many sequential inflations and deflations are needed during a postconditioning, use of an angioplasty catheter has many drawbacks. As a result much time is lost in the process of using a conventional angioplasty catheter for postconditioning.

Use of a conventional angioplasty catheter can also result in significant operator-to-operator variability in inflation time, pressure of balloon, size of balloon, and deflation time. A system which normalizes the inflation time, pressure, size and deflation time is required, while still allowing operator control of the duration of inflation. Lastly, angioplasty balloons, especially rapid exchange balloons, do not have any means to deliver drug distal to the balloon without the added steps of removing the rapid exchange guidewire and replacing the rapid exchange guidewire with an over-the-wire guidewire.

Therefore, a need exists for a system that is capable of restoring blood flow after an ischemic event in an intermittent and gradual fashion with ease and efficiency, while allowing the option of drug delivery distal to the balloon over a standard length guidewire. Further, there remains a need for an ischemic postconditioning system comprising a catheter and a fluid circuit to control and modulate flow of inflation fluid to and from a balloon wherein balloon can be semi-automatically inflated and deflated. Additionally, a need also exists for safety measures which prevent over inflation of the balloon, thus mitigating the risk of balloon rupture and vessel injury, as described below. The disclosed subject matter includes a method and apparatus for performing ischemic postconditioning in a much shorter time and at significantly reduced risk to the patient than is possible with prior art technology.

Additionally, as mentioned above, PCTA is employed to dilate the ischemic blockage and to restore the blood supply to the tissues and organs when a patient suffers from an obstructed blood vessel, typically as a result of atherosclerosis. During PCTA, an empty (deflated) and collapsed balloon disposed on a catheter is usually passed into the narrowed location of the blood vessel and then inflated to a fixed size. Inflation of the balloon at the narrowed location of the blood vessel compresses the obstruction to open up the blood vessel for improved flow. During the angioplasty procedure, the physician is required to determine whether the balloon is inflated by reviewing the balloon on a monitor or screen usually away from the patient undergoing the treatment. Thus, the physician must be careful enough to maintain the catheter at the lesion and take his view away from the patient to view the screen to make the determination if the balloon is inflated or depend on another to view the monitor. Thus, there is a need for an easy to use balloon catheter having an indicator to indicate to the physician when the balloon is inflated in a manner assures the physician the balloon is inflated without being required to turn away from the patient or make the judgment from a monitor.

SUMMARY OF INVENTION

The purpose and advantages of the present invention will be set forth in and apparent from the description that follows, as well as will be learned by practice of the present invention. Additional advantages of the present invention will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a method of administering ischemic postconditioning comprising providing a catheter, the catheter including an expandable member, e.g. balloon, the catheter configured for use in a variety of vessel sizes, the catheter configured to receive a guidewire of predetermined size. At least one pressure source is provided and coupled with the catheter, with the expandable member disposed in fluid communication with the pressure source. The expandable member is positioned at a predetermined location within a vessel and inflated with an inflation fluid for a period of time, and thereafter deflated to define a reperfusion cycle, which can be repeated as so desired.

Additionally, a therapeutic agent can be delivered simultaneously with postconditioning. Further, the catheter can be configured to receive a rapid exchange guidewire during delivery of the therapeutic agent. The expandable member conforms to the vessel wall having a non-circular cross-section at a pressure of about $2/3$ atmospheres, and is repeatedly inflated for about 30 seconds with an inflation liquid, e.g., $CO_2$.

In accordance with another aspect of the invention, the ischemic postconditioning system comprises a catheter including a plurality of lumens and at least one expandable member. At least one chamber is provided which includes a moveable plunger and a return mechanism, e.g. compression or tension spring, operatively engaged with the plunger, the moveable plunger dividing the at least one chamber into first and second volumes. A first pressure source is provided having a first fluid at a first pressure and is disposed in fluid communication with the first volume of the chamber. A second pressure source is provided having a second fluid at a second pressure and is disposed in fluid communication with the at least one expandable member and the second volume of the chamber. The first fluid supplied by the first pressure source displaces the plunger in a first direction delivering at least a portion of the second fluid into the at least one expandable member. Conversely, the return mechanism displaces the plunger in a second direction delivering the second fluid from the second pressure source to the second volume of the chamber.

The first pressure source is configured to provide fluid at a higher pressure than the second pressure source. Additionally, the amount of expansion of the expandable member is determined by the amount of displacement of the moveable plunger. The displacement of the plunger in the first direction compresses the return mechanism. Furthermore, displacement of the plunger in the first direction decreases the second volume of the chamber, and displacement of the plunger in the second direction increases the second volume of the chamber.

To facilitate deflation of the expandable member, the first volume of the chamber includes at least one exhaust port. Additionally, a check valve is disposed between the chamber and the at least one expandable member with the check valve permitting flow of fluid in one direction. An inflation valve is disposed between the chamber and the first pressure source with the inflation valve actuated by a button or trigger mechanism. An exhaust valve is disposed between the chamber and the at least one expandable member with the exhaust valve diverting flow of fluid away from the at least one expandable member. Similarly, the exhaust valve can be actuated by a button or trigger mechanism. A regulator can be disposed between the second pressure source and the chamber. The pressure of the regulator can be maintained at a constant value, or variably controlled by a switch, valve, or trigger.

In accordance with another aspect of the disclosed subject matter, an ischemic postconditioning system comprises a catheter including a plurality of lumens and at least one expandable member. A first chamber is provided and includes a first moveable plunger and a return mechanism operatively engaged with the plunger, with the at least one expandable member disposed in fluid communication with the first chamber. A second chamber is also provided which includes a second moveable plunger and return mechanism operatively engaged with the second plunger, the at least one expandable member being disposed in fluid communication with the second chamber. At least one pressure source is provided having a fluid disposed therein, with the at least one pressure source disposed in fluid communication with the first and second chambers. The fluid supplied by the at least one pressure source to the first chamber displaces the first plunger in a first direction to inflate the at least one expandable member. Conversely, the fluid supplied by the at least one pressure source to the second chamber displaces the second plunger in a second direction to deflate the at least one expandable member.

In a preferred embodiment, the at least one pressure source includes a first and second pressure source, wherein the first pressure source includes a first fluid at a first pressure disposed in fluid communication with the first and second chambers, and the second pressure source includes a second fluid at a second pressure disposed in fluid communication with the first chamber. In operation, the first return mechanism displaces the first plunger in the second direction delivering the second fluid from the second pressure source to the first chamber. Further, the second moveable plunger of the second chamber is configured as a dual plunger. The fluid supplied by the first pressure source acts on only one portion of the dual plunger, however movement of the first portion of the plunger is synchronized with movement of the second portion of the plunger. Additionally, the second chamber includes at least one exhaust port. Also, a switch valve is disposed between the first pressure source and the chambers, with the switch valve directing flow to one of the first and second chambers.

In accordance with another aspect of the disclosed subject matter, an ischemic postconditioning system comprises a catheter including a plurality of lumens and at least one expandable member and a chamber. The chamber includes a moveable plunger and a return mechanism operatively engaged with the plunger, the at least one expandable member is disposed in fluid communication with the chamber. At least one pressure source is provided having a fluid disposed therein, with the at least one pressure source operatively disposed in fluid communication with the chamber. A valve is also provided, the valve having first and second positions wherein when the valve is in the first position, the at least one pressure source is in fluid communication with the chamber, and when the valve is in the second position, the at least one expandable member is in fluid communication with an exhaust outlet of the valve.

Additionally, the moveable plunger divides the chamber into first and second volumes. The at least one pressure source includes a first and second pressure source wherein the first pressure source includes a first fluid at a first pressure and operatively disposed in fluid communication with the first volume of the chamber. The second pressure source includes a second fluid at a second pressure and operatively disposed in fluid communication with the second volume of the chamber. In operation, the first fluid supplied by the first pressure source displaces the plunger in a first direction delivering at least a portion of the second fluid into the at least one expandable member. The return mechanism displaces the plunger in a second direction delivering the second fluid from the second pressure source to the second volume of the chamber.

Additionally, the valve includes an inlet and outlet, with the inlet disposed in fluid communication with the first pressure source and the outlet disposed in fluid communication with the first volume of the chamber when in the first position. Conversely, the inlet is disposed in fluid communication with the first volume of the chamber and the outlet disposed in fluid communication with the ambient atmosphere when in the second position. The valve permits fluid transfer in a single direction, the direction alternating between inflation and deflation of the expandable member in accordance with the first and second position of the valve. To facilitate deflation of the expandable member, the chamber includes at least one exhaust port.

In one embodiment, the catheter is part of a system for reducing or preventing reperfusion injury to a patient. In this regard, the balloon is preferably a compliant balloon having a length and compliance for sequential inflation and deflation to effectuate postconditioning techniques, such as those described in U.S. Publication 2004/0255956 to Vinten-Johansen et al., the contents of which are incorporated herein by reference thereto. However, the catheter is applicable for use with other applications, such as angioplasty, stent delivery, etc. In this regard, the balloon need not be a compliant balloon or a balloon capable of sequential inflation and deflation. Instead, a typical angioplasty balloon can be employed, as would be known in the art.

In some embodiments, the system includes a safety member to prevent inflation fluid flow. The safety member can be housed in the handle of the system. In this manner, the safety member prevents commencement of inflation fluid flow through the circuit.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF EXEMPLARY EMBODIMENTS

Figure 1:
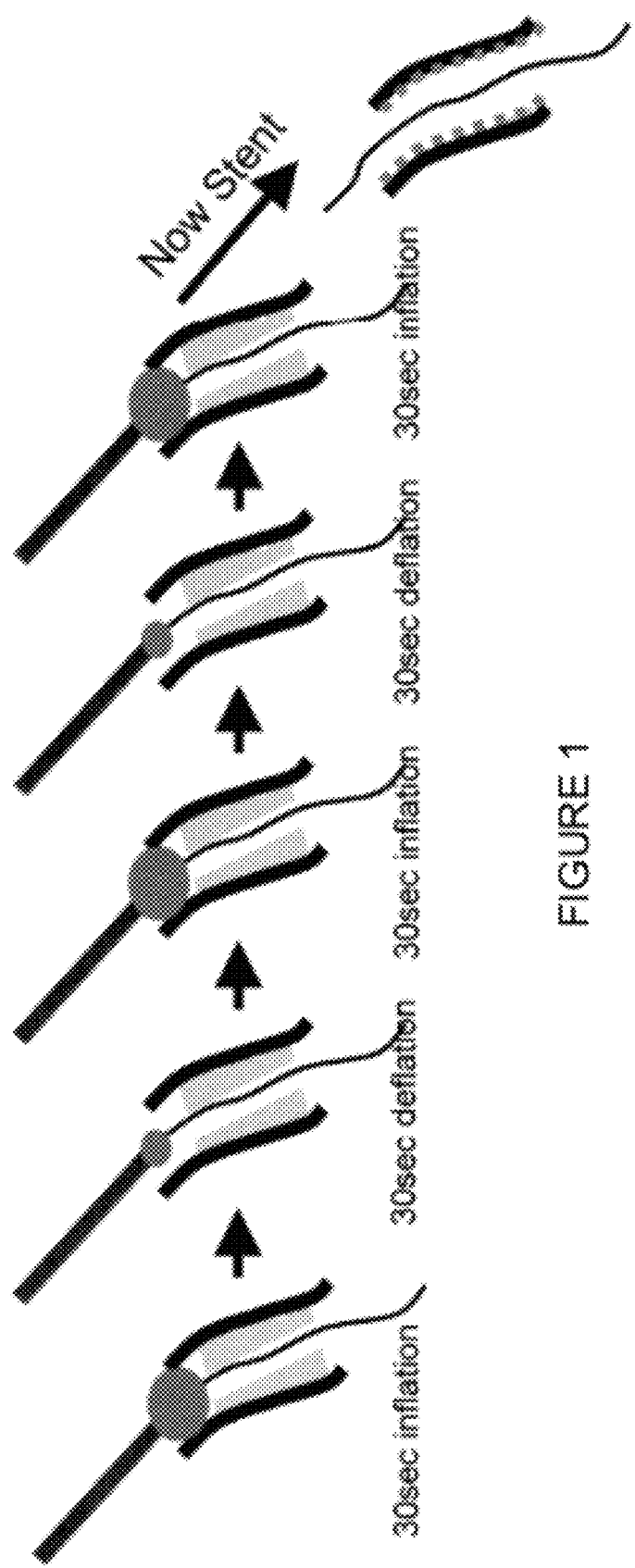
FIGS. 1 and 1A are schematic illustrations of a postconditioning method in accordance with one embodiment of the disclosed subject matter.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims. Where a range of values is provided, it is understood that each intervening value between the upper and lower limit of that range and any other stated or intervening value in that stated range, is encompassed within the disclosed subject matter.

I. System Overview

In accordance with the invention, a system is configured to permit sequential, such as intermittent and repeated, inflation and deflation of an expandable member, such as a balloon. In some embodiments, the sequential inflation and deflation of the balloon is achieved by single-touch actuation. The term "single-touch" as used herein means that actuation of inflation and deflation of the expandable member can be achieved by a single switch, single button, or other single point of actuation. In this regard, the user simply presses or otherwise actuates an actuator to inflate the balloon, and presses it again to actuate deflation of the balloon. Thus, unlike the angioplasty catheter that generally requires sizing, prepping, and inflating by rotation of a screw on the indeflator, one embodiment of the present system avails itself of quick use without the need for preparation.

In this regard, one embodiment of the system provides physicians with an efficient, easy to use catheter designed for rapid, sequential or repeated inflation and deflation of a balloon, such as for reducing or preventing reperfusion injury to an organ or tissue after an ischemic event in the context of preventing or reducing reperfusion injury, or for other applications. For applications in which the system is employed for postconditioning applications, the system can be employed to (1) stop perfusion to the organ or tissue for an amount of time, and (2) permit perfusion to the organ or tissue for another period of time, repeating the stopping and perfusion steps sequentially, and (3) deliver beneficial agents or contrast to areas distal to the balloon.

Beneficial agents include drugs, proteins, therapeutic agents, and other agents that promote health or recovery. Some non-limiting examples include calpain inhibitors, endothelin receptor blockers, pH stabilizing agents, antithrombotic agents, and proteins, cells or vectors including angiogenic factors. Certain non-limiting calpain inhibitors and other beneficial agents are disclosed in WO 98/25899, WO 98/25883, WO 9954305, WO 99/54310, WO 99/61423, WO 00/78933, WO 2008/080969, WO 2009/083581, U.S. Publication Nos. 2006/0205671 and 2008/0097385, each of the disclosures of which are incorporated herein by reference. Other examples of beneficial agents include nitroglycerin, epinepharin, lydocaine, heparin, hirudin, and ReoPro™. As will be recognized in the art, however, other drugs or beneficial agents may be employed.

In one embodiment, the catheter system as described herein is useful for postconditioning methods. In this manner, the expandable member, preferably a balloon, is configured to occlude a blood vessel during expansion or inflation of the expandable member, and then permit resumption of perfusion of the blood flow during contraction or deflation of an expandable member. The occluded vasculature can include a venous blood vessel as in retroperfusion, or an arterial blood vessel such as in reperfusion. The occluded blood vessels may be from the coronary, peripheral, or cerebral vasculature. As illustrated in the schematic of FIG. 1, in one embodiment postconditioning is achieved by inflating and deflating the catheter balloon proximal to a lesion for one or more cycles of about 10 to 60 seconds. These cycles are repeated as necessary to perform the postconditioning therapy. For example, an expandable member is sequentially contracted and expanded such as to permit perfusion for about 10 to about 60 seconds and stop perfusion for about 10 to about 60 seconds for a one or more cycles. In some embodiments, the cycles are repeated for about 3 to about 10 cycles. As shown in FIG. 1, in one embodiment, the cycles for both inflation and deflation are for a period of about 30 seconds each. Other postconditioning methods can be employed, however, such as postconditioning methods described in U.S. Patent Publication No. 2004/0255956 and 2007/0160645 to Vinten-Johansen et al., the disclosures of which is incorporated herein by reference for all purposes. In some embodiments, the catheter is designed to postcondition a stented blood vessel without changing the dimension of the implanted stent. In this manner, the expandable member is a compliant balloon as described below, which does not negatively affect the implanted stent during postconditioning cycles of inflation and deflation of the balloon.

Figure 1A:
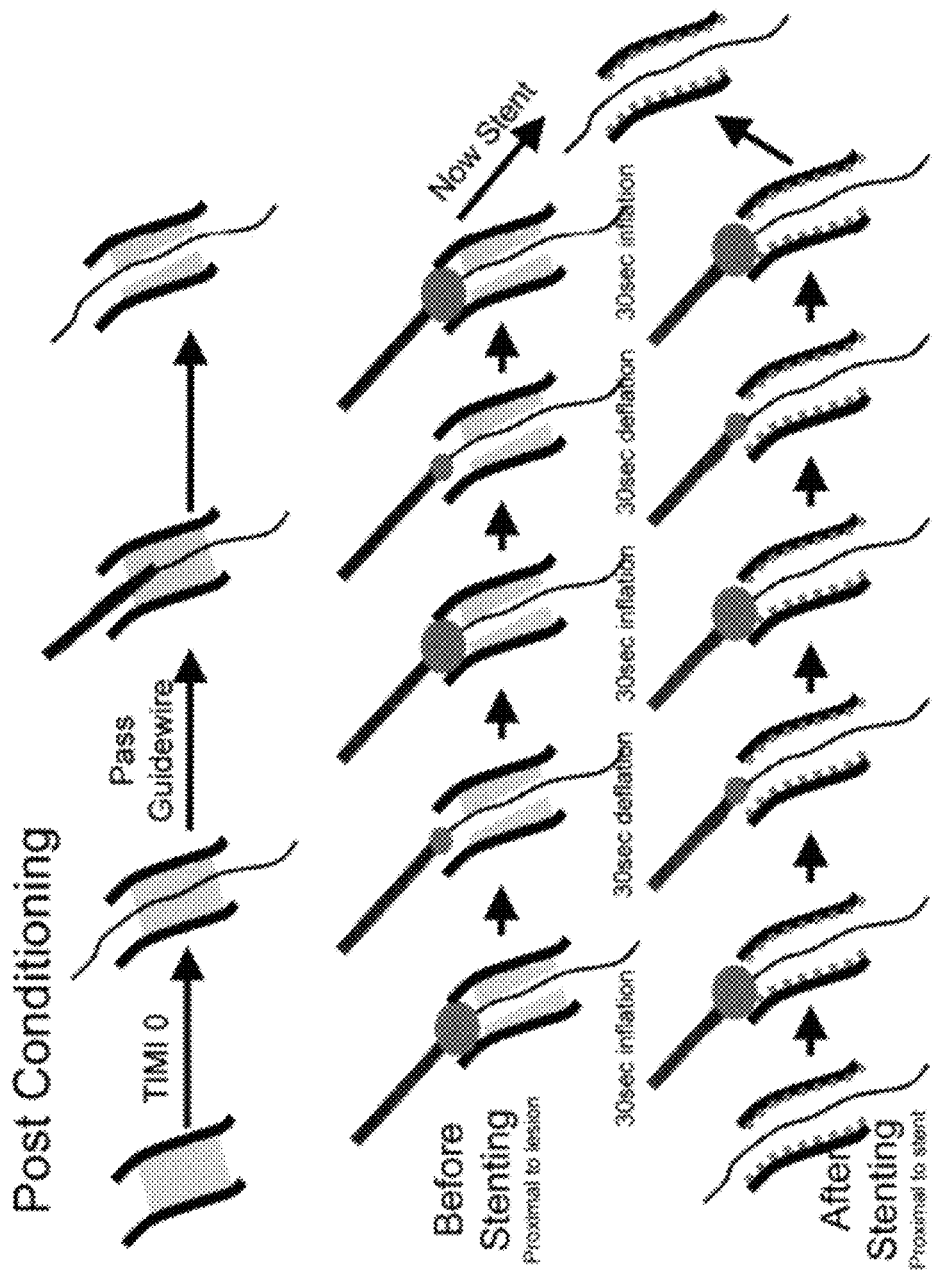

As illustrated in FIG. 1A, the postconditioning technique can be employed prior to stenting a blood vessel or subsequent to stenting a blood vessel. With regards to postconditioning prior to or after stenting, the postconditioning device embodied herein will not dislodge the plaque. With regards to postconditioning after stenting, the postconditioning can occur proximal to the stent, distal to the stent, and/or inside the stent. Advantageously, the catheter device embodied herein does not alter the shape or dimension of the deployed stent when postconditioning is employed within the stented vessel. Accordingly, embodiments of the catheter of the invention can be used for postconditioning before or after placement of a stent in a blood vessel.

In accordance with an aspect of the disclosed subject matter, the catheter system generally includes a catheter including a plurality of lumens and at least one expandable member. At least one chamber is provided which includes a moveable plunger and a return mechanism operatively engaged with the plunger, with the moveable plunger dividing the at least one chamber into first and second volumes. A first pressure source is provided having a first fluid at a first pressure and is disposed in fluid communication with the first volume of the chamber. A second pressure source is provided having a second fluid at a second pressure and is disposed in fluid communication with the at least one expandable member and the second volume of the chamber. In operation, the first fluid supplied by the first pressure source displaces the plunger in a first direction delivering at least a portion of the second fluid into the at least one expandable member. The return mechanism displaces the plunger in a second direction delivering the second fluid from the second pressure source to the second volume of the chamber.

In the exemplary embodiments illustrated in the catheter system generally includes a catheter having an elongate shaft 200, an expandable member 300 and a fluid circuit including a control system 1000. The fluid circuit can be scaled to fit within a housing or handle (not shown), if so desired.

Figure 5A:
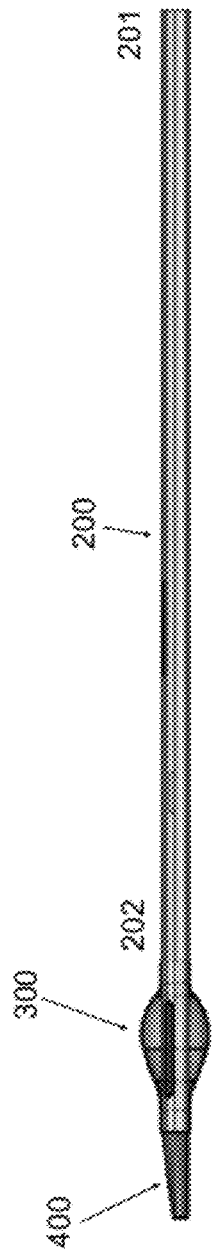
FIGS. 5A-5E are schematic illustrations of the catheter shaft in accordance with embodiments of the disclosed subject matter.
Figure 5C:
Figure 5B:

The elongate shaft 200 includes at least two lumen, as better seen in FIGS. 5A to 5C. In one embodiment, the at least two lumen include an inflation lumen and a separate dedicated independent deflation lumen. Both the inflation lumen and the independent deflation lumen are in fluid communication with the interior portion of a balloon 300. In this regard, an inflation fluid of any pressurized fluid, such as carbon dioxide, noble gases including helium, neon, and pressurized liquids such as saline or contrast agents, is introduced into the balloon 300 via the inflation lumen to inflate the balloon and then exits the balloon via the independent deflation lumen. The independent deflation lumen allows for rapid deflation of the balloon.

As discussed above, the fluid circuit and control system can be housed within a handle, which can be disposed at or near the proximal end of the catheter and houses the control system 1000 of the fluid circuit. The handle can be configured to provide a physician with the ease of automatic, sequential inflation and deflation of expandable member 300 by, in some embodiments, a one-touch actuator. In this manner, the one-touch actuator can be a switch, button, lever, or other device adapted to permit a user to inflate expandable member 300 when actuated in a first position or direction, and to deflate expandable member 300 when actuated in a second position or direction. The one-touch ease of sequential inflation and deflation of expandable member 300 can be achieved by adapting the catheter shaft to include an independent inflation lumen and separate independent deflation lumen. In some embodiments, the switch is configured such that the user cannot overinflate the expandable member 300. In this regard, the system can include a pulse valve that closes an outlet port to the expandable member when the expandable member is fully inflated thereby preventing over inflation. In this manner, when the balloon is fully inflated further actuation of the switch does not further inflate the balloon, thereby rendering the system "fool-proof" and effectuating reproducibility with relation to inflation of the expandable member.

In some embodiments, the control system is configured to assist modulation of inflation fluid flow throughout the fluid circuit of the catheter system such as to effectuate inflation and deflation of the expandable member 300.

II. The Catheter Body

In accordance with one embodiment, as shown FIG. 5A, the catheter includes a generally elongate tubular shaft 200 having a proximal shaft segment 201 and a distal shaft segment 202 in fluid communication. Proximal shaft segment 201 and distal shaft segment 202 can be formed from material having the same or similar hardness or durometer to provide a uniform flexibility along the catheter body. Alternatively, the proximal shaft segment and distal shaft segment can be formed from materials having different flexibilities to provide a catheter having a varied flexibility along a length thereof For example but not limitation, the proximal shaft segment may be formed from a hypotube and the distal shaft can be formed from a polymeric material to provide increased flexibility along the catheter tubular shaft. As such, the proximal shaft and distal shaft segments can be formed from the same tube or alternatively can be two separate tubes connected or welded together to form a unitary tube. The catheter may comprise one or more polymers or polymer blends having different stiffness.

As illustrated in FIG. 5B, elongate shaft 200, in one embodiment, includes an independent inflation lumen 203 configured to provide a passage or flow of inflation fluid to an expandable member 300 disposed at or near the distal end 202 of the catheter shaft. Elongate shaft 200 can also include an independent deflation lumen 206 to provide a second fluid flow passage for the inflation fluid to outflow from expandable member 300 during deflation. In this manner, the sequential inflation and deflation of expandable member 300, and consequential stopping and starting of blood flow during postconditioning techniques can be efficient and rapid. For example, in one embodiment of the system, the expandable member 300 can be inflated in five seconds or less, preferably one second or less, most preferably in 1/15th of a second or less. Further, the expandable member can be deflated in five seconds or less, and preferably three seconds or less, most preferably ¼ of a second or less. This rapid inflation and deflation of the expandable member provides advantages for postconditioning techniques not available through use of the conventional angioplasty catheter.

The elongate shaft 200 can be formed in a number of shapes, for example, in one embodiment, the shaft can have a tubular configuration as shown in FIG. 5B. However, as would be known in the art other shapes can be employed, such as elliptical.

The elongate shaft 200 can further include guidewire lumen 205, for example, in addition to the inflation and deflation lumen. In this regard, guidewire lumen 205 can be configured to extend from a tip 400 at the distal end of elongate shaft 200 to a more proximal location of the elongate shaft 200 to provide an over-the-wire catheter. Alternatively, elongate shaft 200 may be formed to have a notch (not shown) disposed at a location between the distal end 202 and proximal end 201 of elongate shaft 200 to provide a rapid exchange catheter.

In accordance with another embodiment, elongate shaft 200 can further include a drug delivery lumen 204, such as for example, a drug infusion lumen configured to locally deliver beneficial agents such as those described above or other agents. In one embodiment, the beneficial agents are locally delivered to an area of a ischemic event. In other embodiments, the catheter lacks a drug delivery lumen and instead, a drug coated balloon is disposed on the catheter shaft for local delivery of a beneficial agent.

In some embodiments, the elongate shaft 200 includes four separate and independent lumen (e.g., inflation lumen 203, deflation lumen 206, guidewire lumen 205, and drug delivery lumen 204). However, other configurations can be employed. In some embodiments, the diameters of the lumen have different sizes. For example, in some embodiments, the deflation lumen has a diameter of about twice the size of the inflation lumen diameter. In one embodiment, as depicted in FIG. 5C, the diameter of the inflation lumen 203$d$ is about 0.100 mm, the diameter of the deflation lumen 206$d$ is about 0.200 mm, the diameter of the guidewire lumen 205$d$ is about 0.400 mm, and the diameter of the infusion lumen 204$d$ is about 0.300 mm. Accordingly, each lumen can be configured to have a different sized diameter, if desired.

In some embodiments, as illustrated in FIG. 5B, elongate shaft 200 can be formed from a single extrusion with a plurality of lumen, e.g., the four lumen as described above. As further shown, the four lumen can be oriented within the extrusion so that the extruded polymeric web 208 remaining between the lumen forms an "I-beam" cross section. An I-beam configuration provides efficient form for resisting both bending and shear in the plane of the polymeric web 208. In this manner, the plurality of lumen 203, 204, 205, 206 are configured as independent lumen physically spaced from one another by polymeric web 208 disposed therebetween. An advantage of the I-beam shape is that the catheter shaft is more resistant to bending when the catheter is pulled in a particular direction.

Figure 5E:
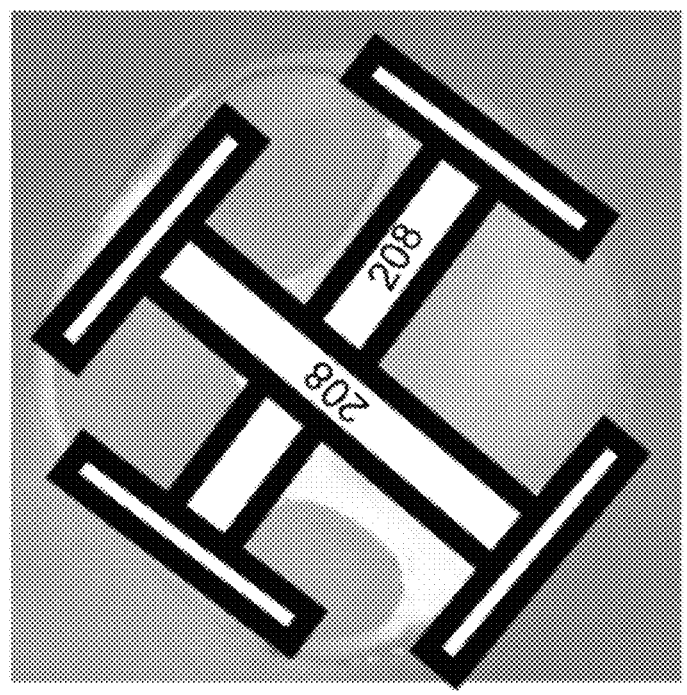
Figure 5D:
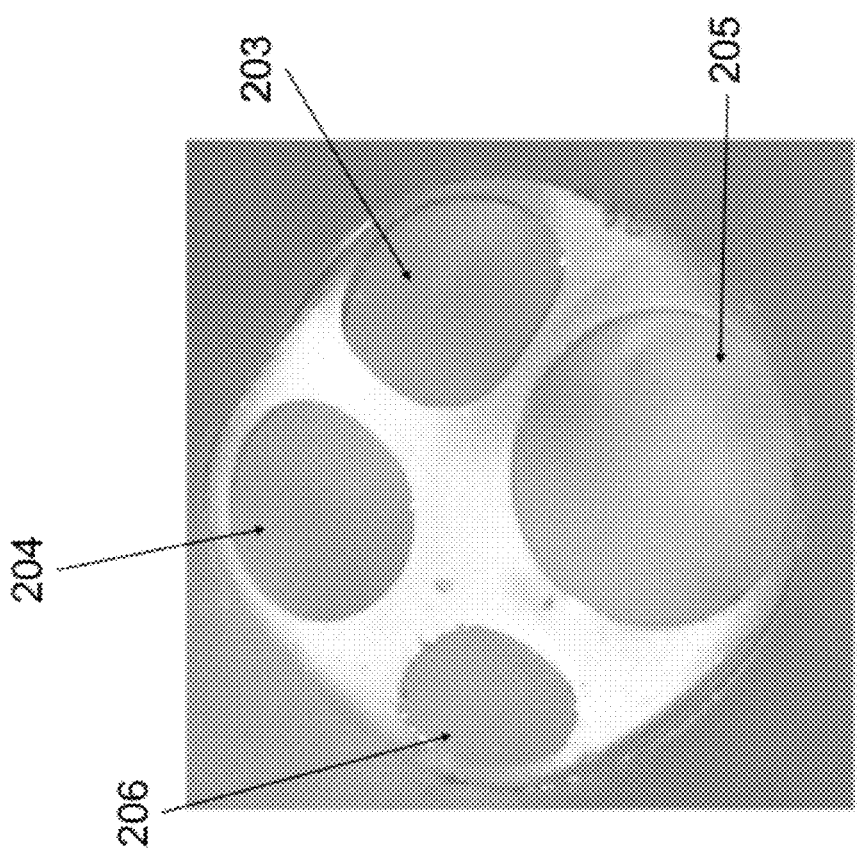

In some embodiments, the different sized lumen are arranged or oriented within the extrusion to form a pattern such that the largest sized lumen 205 is proximate each of the smaller sized lumen 203, 204, 206, as depicted in FIGS. 5B and 5C, such that the polymeric web 208 disposed between the lumen 203, 204 and 205 forms the I-beam pattern, as illustrated in FIGS. 5D and 5E. In some embodiments, the thickness of extruded polymeric web 208 is substantially equivalent to the bending moment of the shaft. A bending moment exists in a structural element when a moment is applied to the element so that the element bends. Moments and torques are generally measured as a force multiplied by a distance so they have as unit newton-meters (N·m), or foot-pounds force (ft-lbf). In this manner, it is believed that the elongate shaft 200 will resist bending equally, regardless of the direction of the bend to the catheter shaft. It is further believed that a catheter shaft without these features will bend to a different degree depending upon the orientation inside the vessel.

Elongate shaft 200 can further include a distal tip 400 (FIG. 5A) having a proximal end abutting or overlapping the distal end 202 of the catheter body. In one embodiment, catheter tip 400 includes one or more lumen. For example, in one embodiment, the tip 400 can include a first lumen aligned with guidewire lumen 205 of elongate shaft 200, and a second lumen aligned with infusion lumen 206. The guidewire lumen 205 is aligned with a lumen through the catheter tip 400 disposed at the distal end of the catheter shaft 202. These aligned lumens permit the catheter to ride over a guidewire. Furthermore, once properly inserted, the guidewire can be removed and fluid can be passed through the lumen.

In one embodiment, the tip 400 can be formed of a material softer than the material of the catheter such that the tip has sufficient column strength to resist buckling during insertion, but is sufficiently flexible to deform when the tip is subjected to axial or radial loads in the body in the absence of the guidewire. Catheter elongate shaft 200 is configured to enable the passage and the longitudinal translation of guidewire within lumen 205 during a surgical procedure.

Elongate shaft 200 can be produced from a variety of materials, including metal, plastic and composite materials. In one embodiment, proximal shaft 201 is manufactured as a metal tube, for example, as a stainless steel hypotube, and may be coated with a polymeric material such as PTFE. The metal tube may also be covered with a single or multilayered plastic material through one or more processes, including coextrusion, dipping, heat-shrinking, and electrostatic and thermal coating. In another embodiment, elongate shaft 200 is manufactured as a plastic tube. Materials suitable for use in the catheter tube include, but are not limited to, Polyurethanes (PU), such as Tecoflex, Pellethene, Bionate, corethane, Elasteon, and blends thereof; Polyethylenes (PE), such as PET, PBT, PVDF, Teflon, ETFE, and blends thereof, Polyolefins, such as HDPE, PE, LDPE, LLDPE, Polypropylene, and blends thereof, Polyimides; Polyamides; all classes of Nylons, such as Nylon 11, Nylon 12, Nylon 6,6, Nylon 6, Nylon 7,11, Nylon 11,12, and blends thereof); block copolymers; PEBA-types polymers, such as ELY, PEBAX, Ubesta, and blends thereof, and biodegradable polymers.

Suitable materials also include blends of the above mentioned materials as well as any composite materials, like dual-layers, tri-layers and multi-layers thereof. For example, catheter shaft may be produced from a tube comprising an outer layer made of Nylon and an inner layer made of a lubricious material such as polyethylene or PTFE. A metallic or nonmetallic braiding may also be included within or between layers of the catheter shaft.

Catheter tip 400 can be configured to provide atraumatic contact between elongate shaft 200 and a wall against which elongate shaft 200 may be pushed during a surgical procedure. The catheter tip can be configured as a soft tip, which in some embodiments, can be composed of a soft sleeve that is affixed on and that extends beyond distal end 202, or, alternatively, that is affixed on and extends beyond the lumen of elongate shaft 200. Typically, a soft tip is affixed through a welding process, but other affixing techniques are also included within the scope of the present invention, for example, adhesive bonding. Suitable materials for the sleeve can be chosen from any material suitable for producing elongate shaft 200. The sleeve may be manufactured from a material softer than elongate shaft 200, and may be formed from the same material as expandable member 300 or from a different material, for example, from any of the materials or combinations of materials described with reference to elongate shaft 200. In one embodiment, the sleeve is manufactured from a material having the same basic composition as, but a lower Shore durometer hardness than, the expandable member 300 material or the elongate tube 200 material. In another embodiment, the sleeve may be manufactured from a blend of PEBAX 55D and PEBAX 63D polymers. One skilled in the art will recognize that the sleeve may be manufactured from a variety of other materials according to the previous description of materials, for example, a polyurethane, a polyethylene, a polyolefin, a polyimide, a polyamide like Nylon, a block copolymer, or blends, or compositions or dual layers or multi-layers thereof.

III. The Expandable Member

In accordance with one embodiment of the invention, expandable member 300 is a polymeric balloon. Preferably, balloon 300 is a compliant balloon. Unlike a typical angioplasty balloon, which is configured to provide a new circular, open lumen, the polymeric balloon 300 of the embodiment should be sufficiently compliant to mold to the anatomy of the blood vessel. In this manner, balloon 300 can occlude a blood vessel having a diameter from about 2 mm to about 30 mm depending on whether the application is for the coronary, cerebral or peripheral blood vessels. In one embodiment, the balloon can occlude a blood vessel having a diameter from about 2 to about 4.5 mm for coronary or cerebral applications, with a pressure of about 0.5 to 2 atm. For peripheral applications, the balloon can occlude a blood vessel having a diameter from about 4 to about 30 mm, or any luminal orifice of the human body where occlusion of fluid flow could be therapeutic.

In one embodiment, the balloon is a one-size-fits-all balloon. In this regard, the balloon must be formed from a compliant polymeric material. For example and not limitation, the compliant balloon 300 can elongate when it is inflated within a narrow sized vessel, and can have a spherical shape when it inflated within a larger or wider blood vessel. Thus, the balloon is capable of molding to the blood vessel. Accordingly, the physician does not need to measure the artery of a patient prior to postconditioning to size balloon 300 to the patient.

In one embodiment, balloon 300 is mounted to elongate shaft 200 of the catheter. Balloon 300 contains a hollow interior portion defining an inflation passage extending longitudinally therethrough to receive inflation fluid from inflation lumen 203 of elongate shaft 200. In one embodiment, the proximal portion of balloon 300 can be configured to taper radially inward at the proximal end and distal end of balloon 300. The proximal end and the distal end of balloon 300 are sized to mount and seal to respective portions of elongate shaft 200, while the balloon interior portion is configured for selective inflation from an unexpanded first condition to an expanded second condition as shown in FIG. 6B. Hence, the transverse cross-sectional dimension of balloon 300, in the expanded condition, is significantly greater than that of the inwardly tapered end portions of proximal end and the distal end of the balloon.

When balloon 300 is mounted to elongate shaft 200, inflation lumen 203 of elongate shaft 200 is in fluid communication with the inflation passage of balloon 300. Accordingly, by operating the one-touch control system at the proximal end of the catheter system, described below, the interior portion of the expandable member 300 can be selectively inflated from the first condition to the inflated second condition.

Distal shaft 202 of the elongate shaft 200 extends through the inflation passage of balloon 300, where a distal end of the catheter terminates distal to the distal end of the balloon 300. As best shown in FIG. 5A, distal shaft 202 extends longitudinally through the interior portion of the balloon 300, and defines the distal portion of the guidewire lumen 205 where it terminates at a distal port at a distal end of the elongate shaft 200. Hence, a guidewire (not shown) may extend through guidewire lumen 205 of the elongate shaft 200, and out through the distal port of the catheter distal end. This passage enables the catheter to be advanced along the guidewire that may be strategically disposed in a vessel.

Figure 6A:
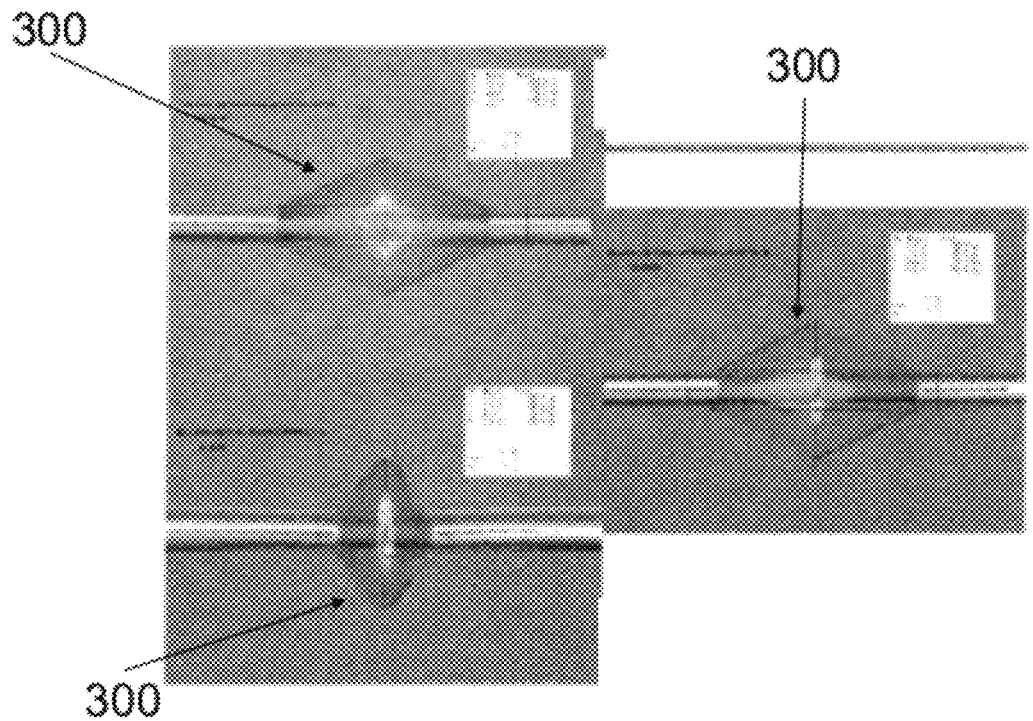
FIGS. 6A and 6B are perspective views of embodiments of balloons in accordance with the disclosed subject matter.
Figure 6B:
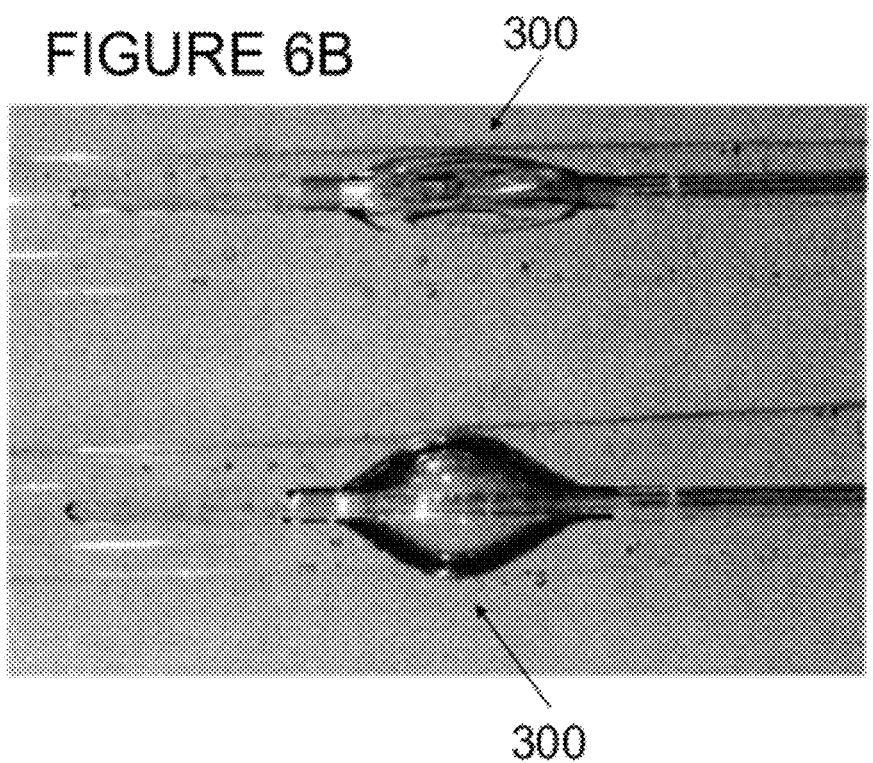

Balloon 300 can be formed in various shapes, as illustrated in FIGS. 6A and 6B. As shown, the shape of balloon 300 can be spherical, cylindrical, or polygonal. Various polymers may be selected for the formation of balloon 300, as would be known in the art. However, the balloon material should be sufficiently compliant such that balloon 300 can mold to the shape of the blood vessel.

In one embodiment, balloon 300 may be formed from a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065D is presently preferred, and has a Shore durometer of 65D, an elongation at break of about 300%, and a high tensile strength at yield of about 10,000 psi. However, other suitable grades may be used, including TECOTHANE® 1075D, having a Shore hardness of about D75. Other suitable compliant polymeric materials include ENGAGE® (DuPont Dow Elastomers (an ethylene alpha-olefin polymer) and EXACT® (Exxon Chemical), both of which are thermoplastic polymers, elastomeric silicones, and latexes.

The compliant material may be crosslinked or uncrosslinked. The presently preferred polyurethane balloon materials are not crosslinked. By crosslinking the balloon compliant material, the final inflated balloon size can be controlled.

Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure.

In one embodiment, balloon 300 is formed from a low tensile set polymer such as a silicone-polyurethane copolymer. Preferably, the silicone-polyurethane is an ether urethane and more specifically an aliphatic ether urethane such as PURSIL AL 575A and PURSIL AL10 (Polymer Technology Group), and ELAST-EON 3-70A (Elastomedics), which are silicone polyether urethane copolymers, and more specifically, aliphatic ether urethane cosiloxanes.

In an alternative embodiment, the low tensile set polymer is a diene polymer. A variety of suitable diene polymers can be used such as but not limited to an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. The diene polymer can be an isoprene including isoprene copolymers and isoprene block copolymers such as poly(styrene-block-isoprene). A presently preferred isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the invention include HT 501 available from Apex Medical, and neoprene (i.e., polychloroprene) available from Dupont Elastomers, including Neoprene G, W, T and A types available from Dupont Elastomers.

In one embodiment, the polymeric material is a compliant material such as, but not limited to, a polyamide/polyether block copolymer (commonly referred to as PEBA or polyether-block-amide). Preferably, the polyamide and polyether segments of the block copolymers may be linked through amide or ester linkages. The polyamide block may be selected from various aliphatic or aromatic polyamides known in the art. Preferably, the polyamide is aliphatic. Some non-limiting examples include nylon 12, nylon 11, nylon 9, nylon 6, nylon 6/12, nylon 6/11, nylon 6/9, and nylon 6/6. Preferably, the polyamide is nylon 12. The polyether block may be selected from various polyethers known in the art. Some non-limiting examples of polyether segments include poly(tetramethylene glycol), tetramethylene ether, polyethylene glycol, polypropylene glycol, poly(pentamethylene ether) and poly(hexamethylene ether). Commercially available PEBA material may also be utilized such as for example, PEBAX® materials supplied by Arkema (France). Various techniques for forming a balloon from polyamide/polyether block copolymer are known in the art. One such example is disclosed in U.S. Pat. No. 6,406,457 to Wang, the disclosure of which is incorporated by reference.

In another embodiment, the balloon material is formed from polyamides. Preferably, the polyamide has substantial tensile strength, is resistant to pin-holing even after folding and unfolding, and is generally scratch resistant, such as those disclosed in U.S. Pat. No. 6,500,148 to Pinchuk, the disclosure of which is incorporated herein by reference. Some non-limiting examples of polyamide materials suitable for the balloon include nylon 12, nylon 11, nylon 9, nylon 69 and nylon 66. Preferably, the polyamide is nylon 12. In yet another embodiment, balloon 300 is composed of several different layers, each one being a different polyamide or polyamide/polyether block copolymer.

In accordance with some embodiments, balloon 300 can be composed of a single polymeric layer, or alternatively, can be a multilayered balloon, such as those described in U.S. Pat. No. 5,478,320 to Ishida, U.S. Pat. No. 5,879,369 to Trotta, or U.S. Pat. No. 6,620,127 to Lee, the disclosures of which are incorporated herein by reference.

IV. The Fluid Circuit

As described above, the catheter system can include a handle generally disposed at or near the proximal end of the catheter. The handle can include a housing of various shapes and configurations.

The fluid circuit generally includes the inflation and independent deflation lumen disposed along the catheter shaft 200, a control system disposed in the handle, if provided, and a plurality of valves to control and regulate pulsated and/or modulated flow of inflation fluid through the catheter system, as described below.

In some embodiments, elongate shaft 200 includes an inlet port and an outlet port. Inflation fluid is delivered to the inlet port from a pressurized reservoir as part of the control system of the fluid circuit. The inflation fluid flows through inflation lumen 203 of elongate shaft 200, enters the interior portion of the expandable member 300 via an inlet port. The inflow of the inflation fluid into the interior of expandable member 300 causes it to inflate and occlude the blood flow in the artery when disposed therein. An outlet port disposed on the elongate shaft 200 facilitates deflation of expandable member 300 by providing an opening for the inflation fluid to flow from expandable member 300 to deflation lumen 206 during deflation.

Figure 2:
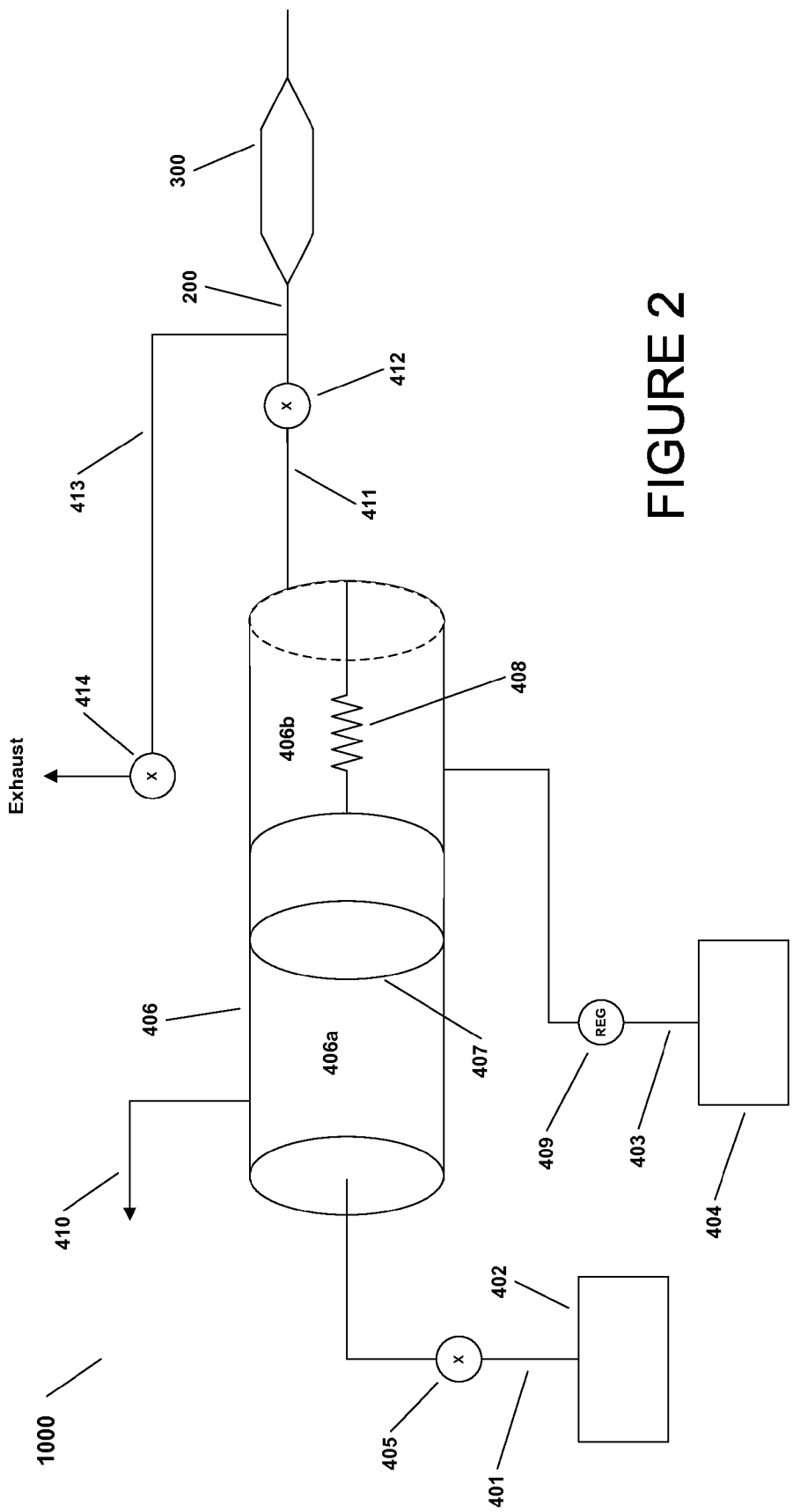
FIG. 2 is a schematic representation of the fluid circuit of the system in accordance with one embodiment of the disclosed subject matter.

In the exemplary embodiment illustrated in FIG. 2, the fluid circuit and control system 1000 includes a first pressurized reservoir 402 containing a working fluid, and a second pressurized reservoir 404 containing an inflation fluid. The reservoirs 402, 404 are provided with differing pressures, preferably with the first (i.e. working fluid) reservoir 402 having a higher pressure than the second (i.e. inflation fluid) reservoir 404 such that the working fluid is employed to drive the inflation fluid into the balloon, as discussed below. The working fluid and inflation fluid can be various fluids known in the art. For example, the fluids can be a gas fluid or a liquid fluid. Further, the working fluid can be a different fluid than the inflation fluid, or alternatively the fluids can be provided with the same composition, if so desired. For the purpose of illustration, the working fluid and inflation fluid can be carbon dioxide or saline.

A chamber 406 is provided in fluid communication with the working fluid reservoir 402 and the inflation fluid reservoir 404 via inlet tubing lines 401 and 403, respectively. In the illustrated embodiment, the chamber 406 is configured as a cylindrical body, e.g. a syringe barrel, although alternative configurations can be employed as so desired. The chamber 406 houses a moveable plunger 407 which can be arranged as a disk-like member forming a fluid-tight seal between the circumference of the plunger and the inner wall of the syringe chamber 406. Accordingly, the plunger 407 effectively divides the chamber 406 into two volumes, i.e. a proximal volume 406a and a distal volume 406b measured with respect to the plunger 407. A return mechanism 408, e.g. a compression spring, is coupled to the moveable plunger 407 and provides a bias load on the plunger 407 and chamber wall to urge the plunger in a predetermined, e.g. proximal, direction. In the equilibrium position, the return mechanism 408 is substantially extended, as shown in FIG. 2. The amount of bias provided by the return mechanism 408 can be scaled as so desired according to the pressure of the reservoirs, density of the working and inflation fluids, dimensions of the chamber and surface area of the plunger 407 in order to achieve the desired displacement of the plunger 407. In the configuration shown in FIG. 2, the plunger 407 is moved in a distal direction upon application of a load supplied by the working fluid, which in turn compresses the return mechanism 408, as described in further detail below.

An exhaust port 410 can be included in the chamber wall to allow venting of the working fluid from the proximal volume 406a in order to facilitate deflation of the balloon. Although a single exhaust port 410 is illustrated, additional exhaust ports can be provided as so desired in order to expedite the venting and deflation cycle.

An inflation valve 405, which can be operated by the actuator as described above, is included in inlet tubing 401 and positioned between chamber 406 and the working fluid reservoir 402. The inflation valve 405 includes an open position which allows flow of the working fluid to be delivered via inlet tubing 401 into the proximal volume 406a of the chamber 406. Additionally, a regulator 409 is included in inlet tube 403 and positioned between the inflation fluid reservoir 404 and the distal volume 406b of the chamber. The regulator 409 can be preset to a fixed pressure, or alternatively can be variably controlled by a switch, valve or trigger mechanism. A check valve 412 is included in inflation tube 411, which couples the chamber 406 to the balloon 300 via the inflation lumen 203 of the catheter. The check valve 412 is disposed between the chamber and the balloon and configured to permit fluid flow in only a single direction, i.e. distally from the chamber into the balloon. The check valve 412 can be configured with a crack pressure, e.g. 1.5 atmospheres, sufficient to withstand minor pressure fluctuations in the fluid circuit such that the valve only opens when an inflation cycle is commanded by the operator.

An exhaust conduit or tubing line 413 is arranged in fluid communication with the balloon. Also included in the exhaust line 413 is an exhaust check valve 414 which has an outlet to the ambient atmosphere to allow the inflation fluid to exit from the balloon to the surrounding atmosphere upon deflation of the balloon.

In operation, the catheter and balloon are coupled to the fluid circuit of FIG. 2 with the balloon preferably in a low profile state, e.g. at least partially collapsed or unexpanded. A predetermined volume of inflation fluid is delivered or loaded into the distal volume 406b of the chamber. The user then actuates the inflation valve 405, via the trigger mechanism described above, to allow working fluid to be delivered from reservoir 402 into the proximal volume 406a of the chamber. As discussed above, the working fluid is supplied at a higher pressure than the inflation fluid such that as the working fluid fills the volume 406a, the pressure imparted on the moveable plunger 407 causes displacement of the plunger in a distal direction. Thus, the proximal volume 406a is increased while the distal volume 406b is decreased proportionally. Consequently, the inflation fluid present in the distal volume 406b is forced through the inflation line 411, through the check valve 412, through the inflation lumen 203 of the catheter, and into the balloon 300 to thereby expand the diameter of the balloon. The amount of expansion of the balloon is determined by the amount of inflation fluid forced out of the distal volume 406b, which in turn is determined by the amount of inflation fluid delivered to the proximal volume 406a.

When the inflation valve 405 is closed, the working fluid in the proximal volume 406a of the chamber is allowed to exit through the exhaust port 410 thereby reducing the pressure imparted on the moveable plunger 407. Once the pressure on the proximal face of the plunger 407 is lower than the bias provided by the return mechanism 408, the plunger will retract in a proximal direction and return to its starting position. Consequently, the proximal volume 406a will decrease while the distal volume 406b will increase proportionally. The increase in volume of the distal volume 406b will lower the pressure in the distal volume 406b. When the pressure in the distal volume 406b reduces to a level below the pressure of the reservoir 404, inflation fluid will transfer from the reservoir 404 through the regulator and into the distal volume 406b. This effectively reloads or recharges the chamber for another reperfusion cycle. This process can be repeated to perform as many reperfusion cycles as so desired.

Deflation of the balloon 300 can begin immediately after the inflation phase is completed, i.e., the increase in the balloon pressure above the crack pressure of the exhaust check valve 414 can force the inflation fluid to exit valve 414 to the ambient environment. Accordingly, the crack pressure of the exhaust check valve 414 can be set at a predetermined level which allows exhausting of gas to achieve partial deflation of the balloon sufficient to reduce the balloon profile to permit perfusion of blood through the vessel. The particular exhaust check valve pressure can be set according to the amount of deflation and corresponding perfusion desired. Further, the exhaust check valve 414 serves as a safety measure against over inflation of the balloon since any additional inflation fluid delivered above the crack pressure will bleed off through the exhaust valve 414, rather than be introduced into the balloon 300. Additionally, or alternatively, full deflation of the balloon can be achieved by incorporating a manual release mechanism in the exhaust valve 414 such that, upon pressing a button for example, the valve would open and allow the balloon to deflate to a minimum diameter.

Figure 3:
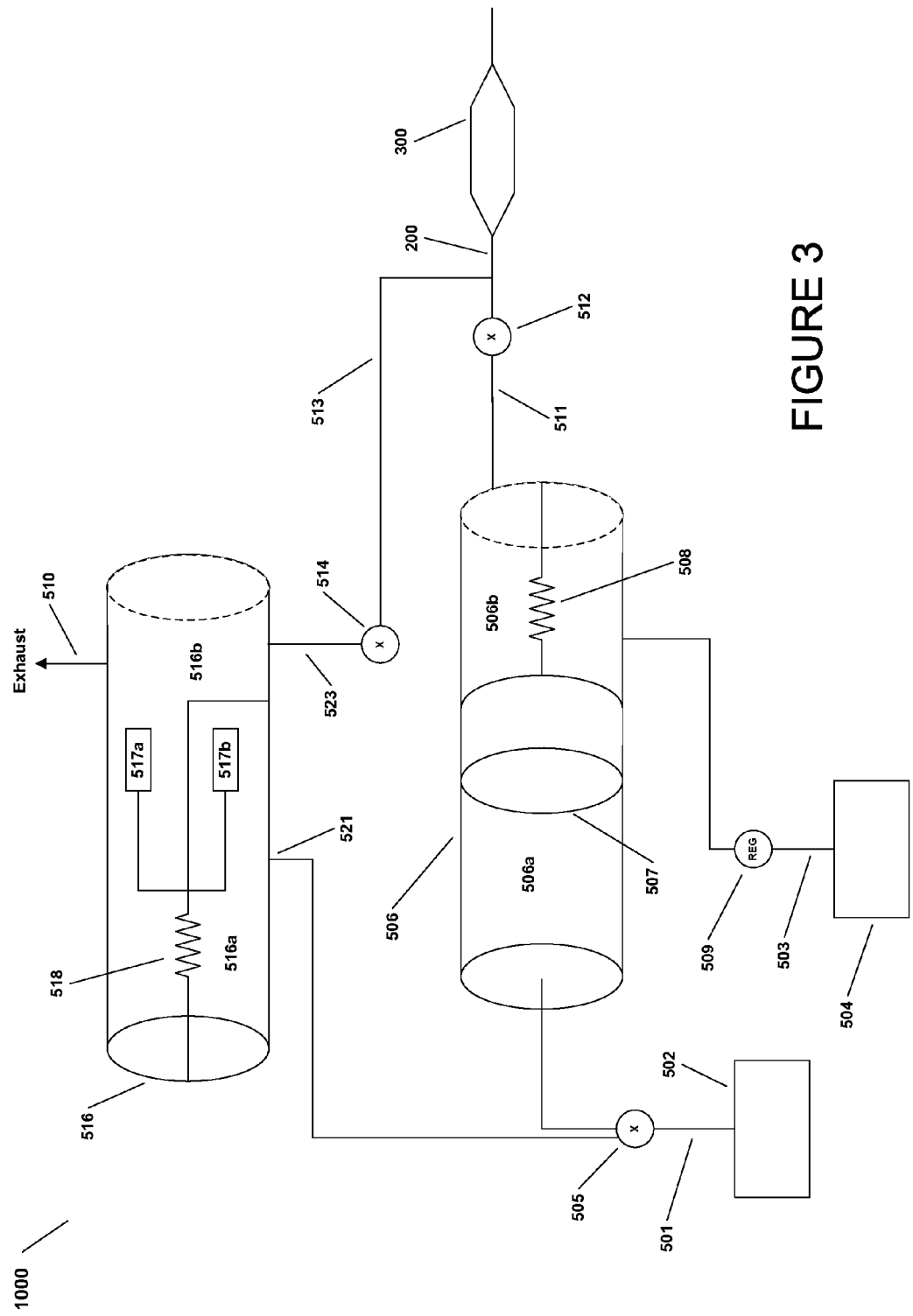
FIG. 3 is a schematic representation of the fluid circuit of the system in accordance with another embodiment of the disclosed subject matter.

In accordance with another exemplary embodiment, as shown in FIG. 3, a plurality of chambers 506, 516 can be employed in the fluid circuit 1000 wherein the first chamber 516 functions as an inflation chamber, and the second chamber 516 functions as a deflation chamber. The first chamber 506, working fluid reservoir 502, inflation fluid reservoir 504, and exhaust check valve 512 are constructed and operate in accordance with the embodiment illustrated in FIG. 2 as described above. Thus, similar reference numerals are provided to refer to similar components between the two embodiments. As shown in FIG. 3, the second chamber 516 is constructed with a dual plunger 517a, 517b configuration wherein the plungers are coupled together such that movement of one plunger is synchronized with movement of the other. The second chamber 516 is configured with an inlet port 521 in fluid communication with the inlet line 501 to receive working fluid from reservoir 402. Additionally, the second chamber 516 is configured with an inlet port 523 which is in fluid communication with the exhaust line 513 to receive inflation fluid from the balloon 300. The inlet ports 521, 523 are arranged on one side (e.g. within the distal volume 56b) of the chamber with the return mechanism 518 disposed on the opposite side (e.g. within the proximal volume 516a) of the chamber. However, if a tension spring were employed as the return mechanism instead of the compression spring 518 illustrated, the inlet ports 521, 523 would be located within the same side of the chamber. The second chamber 516 is also configured with an exhaust port 510 to allow venting or exhaust of the inflation fluid to the ambient atmosphere.

In operation, the fluid circuit illustrated in FIG. 3 functions as a single-throw two-pole switch by directing the working fluid from the high pressure reservoir 502 either into the inflation chamber 506 or the deflation chamber 516. The catheter and balloon 300 are coupled to the fluid circuit of FIG. 3 with the balloon preferably in a low profile state, e.g. at least partially collapsed or unexpanded. A predetermined volume of inflation fluid is delivered or loaded into the distal volume 506b of the inflation chamber 506. The user then actuates the inflation, i.e. switch, valve 505 via the trigger mechanism described above, to allow working fluid to be delivered from reservoir 502 into the proximal volume 506a of the inflation chamber 506. As discussed above, the working fluid is supplied at a higher pressure than the inflation fluid such that as the working fluid fills the volume 506a, the pressure imparted on the moveable plunger 507 causes displacement of the plunger in a distal direction. Thus, the proximal volume 506a is increased while the distal volume 506b is decreased proportionally. Consequently, the inflation fluid present in the distal volume 506b is forced through the inflation line 511, through the check valve 512, through the inflation lumen 203 of the catheter, and into the balloon 300 to thereby expand the diameter of the balloon. The amount of expansion of the balloon is determined by the amount of inflation fluid forced out of the distal volume 506b, which in turn is determined by the amount of inflation fluid delivered to the proximal volume 506a.

When the inflation valve 505 is switched closed, the working fluid is directed towards the deflation chamber 516. One of the plungers 517a, 517b is exposed to the working fluid such that during the deflation phase the working fluid imparts a pressure on the surface of the plunger to cause displacement in a proximal direction. Due to the coupling and synchronization of the plungers 517a, 517b, the second plunger will also be displaced in a proximal direction thereby creating a vacuum draw in the distal volume 516b of the deflation chamber. Consequently, inflation fluid will be drawn from the balloon 300 through the exhaust valve 514 and into the deflation chamber. The inflation fluid withdrawn from the balloon 300 is allowed to escape or exhaust to the ambient atmosphere through exhaust port 510 provided in the distal volume 516b of the deflation chamber 516. Additionally, proximal volume 506a of the inflation chamber includes an exhaust port for releasing the fluid contained therein.

The reduction of inflation fluid in distal volume 516b thereby reduces the pressure imparted on the moveable plunger 517a, 517b. Once the pressure on the distal face of the plunger 517a, 517b is lower than the bias provided by the return mechanism 518, the plunger will advance in a distal direction and return to its starting position. This restoration or return of the plunger 517a, 517b in the deflation chamber occurs during the subsequent inflation phase, when the working fluid is delivered to the inflation chamber 506.

Figure 4:
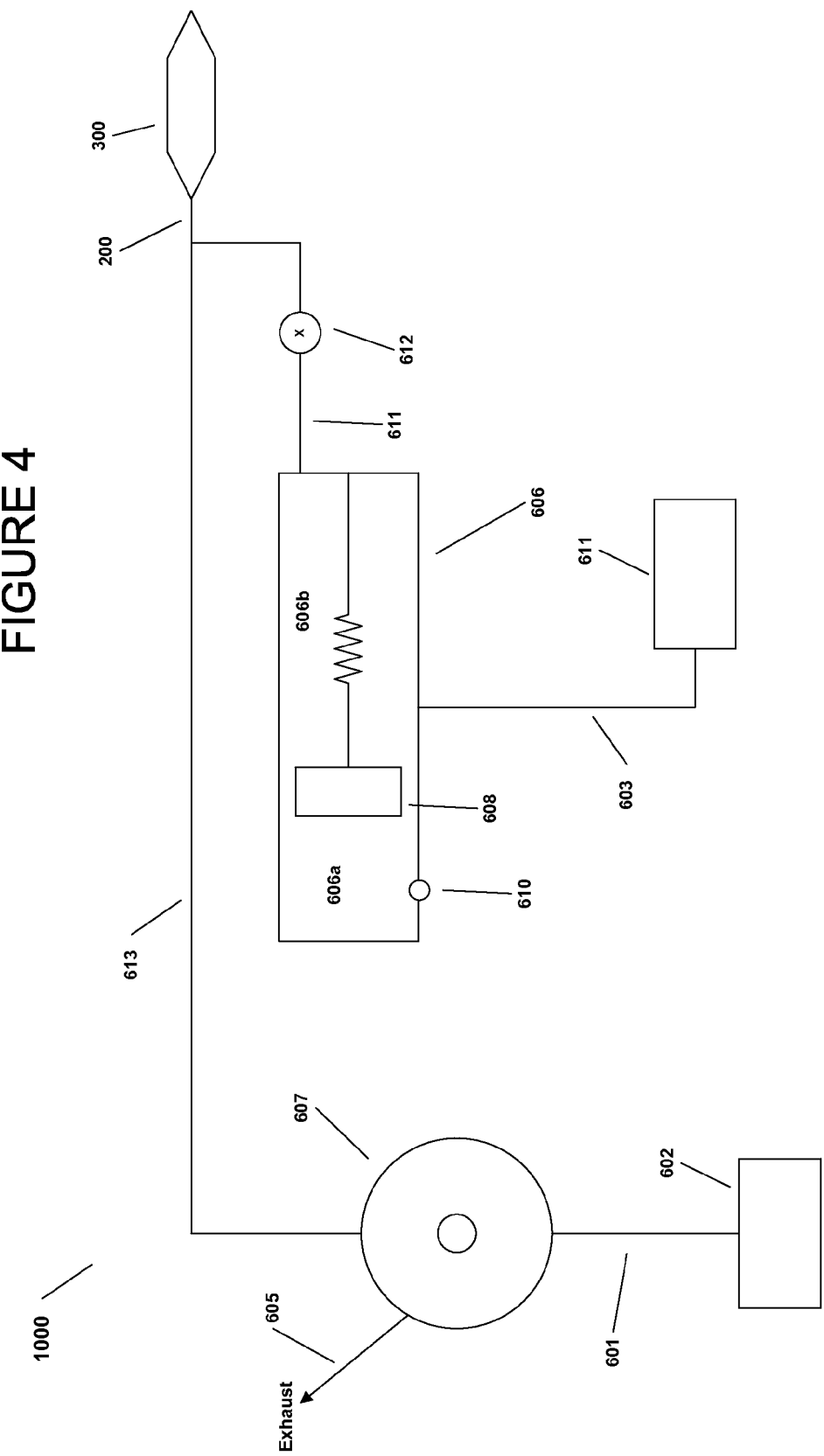
FIG. 4 is a schematic representation of the fluid circuit of the system in accordance with another embodiment of the disclosed subject matter.

In accordance with another exemplary embodiment of the fluid circuit, as shown in FIG. 4, a single chamber 606 is provided and a multi-way pneumatic switch valve is provided which allows the inlet and outlet of the valve to be switched between two positions, a first for inflation and a second for deflation of the balloon. The chamber 606, working fluid reservoir 602, inflation fluid reservoir 604, and exhaust check valve 612 are constructed and operate in accordance with the embodiment illustrated in FIG. 2 as described above. Thus, similar reference numerals are provided to refer to similar components between the two embodiments. Additionally, the exhaust line 613 extends from the balloon 300 to the switch valve 605 such that the balloon and switch valve 605 are in direct fluid communication.

When the switch valve 605 is in the first or inflation position, the valve inlet is coupled to the working fluid reservoir 602, and the valve outlet is coupled to the proximal volume 606a of the chamber 606. When the switch valve 605 is in the second or deflation position, the valve inlet is coupled to the exhaust line 613 of the balloon, and the exhaust valve 612, while the valve outlet is exposed to ambient atmosphere such that the fluid can exit from the balloon 300 through the circuit 1000 to ambient surroundings. Further, the switch valve 605 is constructed such that when the valve is in a given position, i.e. inflation or deflation, only the ports of the circuit 1000 which are coupled to the inlet and outlet of the valve are operational, while the uncoupled ports are closed off For example, when the switch valve 605 is in the inflation position, fluid is allowed to transfer from the working reservoir 602 into the chamber 606 and inflation fluid is allowed to transfer from the chamber into the balloon, however fluid transfer from the balloon 300 to the valve 605 (via exhaust line 613) is not permitted. Accordingly, the circuit 1000 illustrated in FIG. 4 is configured to alternate the direction of fluid flow based on the switch valve 605 position.

In operation, the catheter and balloon are coupled to the fluid circuit of FIG. 4 with the balloon preferably in a low profile state, e.g. at least partially collapsed or unexpanded. The switch valve 605 is provided in the exhaust position. A predetermined volume of inflation fluid is delivered or loaded into the distal volume 606b of the chamber. The user then actuates or switches the valve 605 to the inflation position, via a trigger mechanism described above, to allow working fluid to be delivered from reservoir 602 into the proximal volume 606a of the chamber. As discussed above, the working fluid is supplied at a higher pressure than the inflation fluid such that as the working fluid fills the volume 606a, the pressure imparted on the moveable plunger 607 causes displacement of the plunger in a distal direction. Thus, the proximal volume 606a is increased while the distal volume 606b is decreased proportionally. Consequently, the inflation fluid present in the distal volume 606b is forced through the inflation line 611, through the check valve 612, through the inflation lumen 203 of the catheter, and into the balloon 300 to thereby expand the diameter of the balloon. The amount of expansion of the balloon is determined by the amount of inflation fluid forced out of the distal volume 606b, which in turn is determined by the amount of inflation fluid delivered to the proximal volume 606a.

When the switch valve 605 is moved to the exhaust position, the working fluid in the proximal volume 606a of the chamber is allowed to exit through the exhaust port 610 thereby reducing the pressure imparted on the moveable plunger 607. Once the pressure on the proximal face of the plunger 607 is lower than the bias provided by the return mechanism 608, the plunger will advance in a proximal direction and return to its starting position. Consequently, the proximal volume 606a will decrease while the distal volume 606b will increase proportionally. The increase in volume of the distal volume 606b will lower the pressure in the distal volume 606b. When the pressure in the distal volume 606b reduces to a level below the pressure of the reservoir 604, inflation fluid will transfer from the reservoir 604 through the regulator and into the distal volume 606b. This effectively reloads or recharges the chamber for another reperfusion cycle. This process can be repeated to perform as many reperfusion cycles as so desired.

Further, the exhaust check valve 612 is disposed between the balloon 300 and the chamber 606. The check valve 612 prevents backflow of fluid from the balloon towards the chamber 606 during the deflation phase. Accordingly, the only fluid path open during the deflation phase is through exhaust line 613 which is coupled to the valve 605 and exhausts fluid to ambient surroundings.

It is noted that the fluid circuits illustrated in FIGS. 2-4 omit the catheter components to simplify the drawings and aid in the illustration of the fluid circuit and balloon, it is to be understood that the catheter shaft is connected between the balloon 300 and the fluid circuit 1000.

Accordingly, the fluid circuit permits the user to sequentially inflate and deflate the expandable member with the ease of rapid succession. The handle, if provided, may further include a pulse valve to deliver time-controlled, or volume-controlled flow to the balloon 300. In this regard, the second tubular member may include a one-way check valve to lock the pulse valve delivered carbon dioxide in the expandable member 300.

While the disclosed subject matter is described herein in terms of certain preferred embodiments, those skilled in the art will recognize that various modifications and improvements may be made to the disclosed subject matter without departing from the scope thereof Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. An ischemic postconditioning system comprising:
    a catheter, the catheter including a plurality of lumens and at least one expandable member;
    at least one chamber including a moveable plunger and a return mechanism operatively engaged with the plunger, the moveable plunger dividing the at least one chamber into first and second volumes;
    a first pressure source having a first fluid at a first pressure, the first pressure source disposed in fluid communication with the first volume of the chamber;
    a second pressure source having a second fluid at a second pressure, the second pressure source and the at least one expandable member disposed in fluid communication with the second volume of the chamber;
    wherein the first fluid supplied by the first pressure source displaces the plunger in a first direction delivering at least a portion of the second fluid into the at least one expandable member; and
    wherein the return mechanism displaces the plunger in a second direction delivering the second fluid from the second pressure source to the second volume of the chamber.

2. The system of claim 1, wherein the first pressure source provides fluid at a higher pressure than the second pressure source.

3. The system of claim 1, wherein the amount of expansion of the expandable member is determined by the amount of displacement of the moveable plunger.

4. The system of claim 1, wherein the displacement of the plunger in the first direction compresses the return mechanism.

5. The system of claim 1, wherein displacement of the plunger in the first direction decreases the second volume of the chamber, and displacement of the plunger in the second direction increases the second volume of the chamber.

6. The system of claim 1, wherein the first volume of the chamber includes at least one exhaust port.

7. The system of claim 1, wherein the return mechanism is a compression spring.

8. The system of claim 1, further comprising a check valve disposed between the chamber and the at least one expandable member, the check valve permitting flow of fluid in one direction.

9. The system of claim 1, further comprising an inflation valve disposed between the chamber and the first pressure source, the inflation valve actuated by a button or trigger.

10. The system of claim 1, further comprising an exhaust valve disposed between the chamber and the at least one expandable member, the exhaust valve diverting flow of fluid away from the at least one expandable member.

11. The system of claim 10, wherein the exhaust valve is actuated by a button or trigger.

12. The system of claim 1, further comprising a regulator disposed between the second pressure source and the chamber.

13. The system of claim 12, wherein the pressure of the regulator is constant.

14. The system of claim 12, wherein the pressure of the regulator is variably controlled by a switch, valve, or trigger.

15. An ischemic postconditioning system comprising:
a catheter, the catheter including a plurality of lumens and at least one expandable member;
a first chamber, the first chamber including a first moveable plunger and a return mechanism operatively engaged with the plunger, the at least one expandable member disposed in fluid communication with the first chamber;
a second chamber, the second chamber including a second moveable plunger and return mechanism operatively engaged with the second plunger, the at least one expandable member disposed in fluid communication with the second chamber;
at least one pressure source having a fluid disposed therein, the at least one pressure source disposed in fluid communication with the first and second chambers;
wherein the fluid supplied by the at least one pressure source to the first chamber displaces the first plunger in a first direction to inflate the at least one expandable member; and
wherein the fluid supplied by the at least one pressure source to the second chamber displaces the second plunger in a second direction to deflate the at least one expandable member.

16. The system of claim 15, wherein the at least one pressure source includes a first and second pressure source:
wherein the first pressure source includes a first fluid at a first pressure, the first pressure source disposed in fluid communication with the first and second chambers; and
the second pressure source includes a second fluid at a second pressure, the second pressure source disposed in fluid communication with the first chamber.

17. The system of claim 16, wherein the first return mechanism displaces the first plunger in the second direction delivering the second fluid from the second pressure source to the first chamber.

18. The system of claim 15, wherein the second moveable plunger of the second chamber is configured as a dual plunger.

19. The system of claim 18, wherein the fluid supplied by the first pressure source acts on only one portion of the dual plunger.

20. The system of claim 19, wherein movement of the first portion of the plunger is synchronized with movement of the second portion of the plunger.

21. The system of claim 15, wherein the second chamber includes at least one exhaust port.

22. The system of claim 15, further comprising a switch valve disposed between the first pressure source and the chambers, the switch valve directing flow to one of the first and second chambers.

23. An ischemic postconditioning system comprising:
a catheter, the catheter including a plurality of lumens and at least one expandable member;
a chamber, the chamber including a moveable plunger and a return mechanism operatively engaged with the plunger, the at least one expandable member disposed in fluid communication with the chamber;
at least one pressure source having a fluid disposed therein, the at least one pressure source operatively disposed in fluid communication with the chamber;
a valve, the valve having first and second positions;
wherein when the valve is in the first position, the at least one pressure source is in fluid communication with the chamber; and
wherein when the valve is in the second position, the at least one expandable member is in fluid communication with an exhaust outlet of the valve.

24. The system of claim 23, wherein the moveable plunger divides the chamber into first and second volumes.

25. The system of claim 24, wherein the at least one pressure source includes a first and second pressure source:
wherein the first pressure source includes a first fluid at a first pressure, the first pressure source operatively disposed in fluid communication with the first volume of the chamber; and
the second pressure source includes a second fluid at a second pressure, the second pressure source operatively disposed in fluid communication with the second volume of the chamber.

26. The system of claim 25, wherein the first fluid supplied by the first pressure source displaces the plunger in a first direction delivering at least a portion of the second fluid into the at least one expandable member.

27. The system of claim 25, wherein the return mechanism displaces the plunger in a second direction delivering the second fluid from the second pressure source to the second volume of the chamber.

28. The system of claim 25, wherein the valve includes an inlet and outlet:
the inlet disposed in fluid communication with the first pressure source and the outlet disposed in fluid communication with the first volume of the chamber when in the first position;
the inlet disposed in fluid communication with the first volume of the chamber and the outlet disposed in fluid communication with the ambient atmosphere when in the second position.

29. The system of claim 23, wherein the valve permits fluid transfer in a single direction, the direction alternating between inflation and deflation of the expandable member with the first and second position of the valve.

30. The system of claim 23, wherein the chamber includes at least one exhaust port.

* * * * *